US00PP09881P

United States Patent [19]

Janick et al.

[11] Patent Number: Plant 9,881

[45] Date of Patent: May 6, 1997

[54] APPLE TREE 'CO-OP 32'

[75] Inventors: Jules Janick, West Lafayette; Edwin B. Williams, Lafayette; Jeffrey A. Crosby, Lawrenceburg; Paul C. Pecknold, West Lafayette, all of Ind.; Schuyler S. Korban, Champaign, Ill.; Joseph Goffreda, Kendall Park, N.J.

[73] Assignee: Purdue Research Foundation, West Lafayette, Ind.

[21] Appl. No.: 293,700

[22] Filed: Dec. 22, 1995

[51] Int. Cl.[6] ..... A01H 5/00

[52] U.S. Cl. ..... Plt./35.1

[58] Field of Search ..... Plt./35.1

*Primary Examiner*—James R. Feyrer

*Attorney, Agent, or Firm*—Woodard, Emhardt, Naughton, Moriarty & McNett

[57] ABSTRACT

This invention is a new and distinct cultivar of apple tree (*Malus Xdomestica* Borkh). It was discovered in the course of an attempt to develop improved apple cultivars with high fruit quality and resistance to *Venturia inaequalis* (Cke.) Wint., the casual agent of the scab disease of apple. The tree is a seedling of known parentage planted in Apr. 15,1975 in the HF Block of an apple breeding orchard on the Hinsley tract of the Purdue Horticulture Research Farm, West Lafayette, Ind., in row 34. Because the trees in this row were spaced very closely its tree number was not recorded. When selected it had the designation PRI 2946-1 in the breeding records and was tested under the designations HFRow 34 and Co-op 32.

2 Drawing Sheets

BACKGROUND OF THE INVENTION

The present new cultivar, Co-op 32, a new and distinct cultivar of apple tree (*Malus Xdomestica* Borkh.), was a selection from crossing 'Camuzat', a cultivar from Spain, as the seed parent with Co-op 10 (PRI 1659-10=HAR4T132) as the pollen parent in 1974 at the Cream Ridge Research and Development Center, Rutgers University. This new cultivar carries the genetic factor $V_f$ inherited from *Malus floribunda* Sieb 821 that renders it highly resistant to infection caused by *Venturia inaequalis* (Cke.) Wint. The presence of this factor in Co-op 32 has been demonstrated by controlled greenhouse inoculation tests of the seedling and eleven years of observation of the seedling and propagules under natural condition for infection in the field in West Lafayette, Indiana and at multiple sites in the United States. The complete pedigree is shown in FIG. 1.

This new cultivar produces a moderately vigorous spreading tree with good crotch angles with a semi-spur type bearing habit. Co-op 32 is field immune to apple scab. Based on field observations it is moderately resistant to fire blight incited by *Erwinia amylovora* (Burr.) Winslow, and has high resistance to powdery mildew incited by *Podosphaera leucotricha* (Ell. and Ev.) Salm. It is resistant to cedar-apple rust incited by *Gymnosporangium juniperi-virginianae* (Schw.).

Flowering is mid-season to late. The fruit matures very early in the season, 1.5 weeks after 'Lodi' and 'Yellow Transparent' with very good quality and storage life for its season. Quality and shelf-life is significantly better than 'Lodi' or 'Yellow Transparent'.

After observation, the selection was asexually propagated by grafting on seedling, EMLA-111 and EMLA-7 rootstocks, at the Cream Ridge Research and Development Center, Rutgers University. The grafted material has retained the described characteristics after propagation.

BRIEF DESCRIPTION OF THE FIGURES

FIG. 2 is a photograph showing fruit and leaves of Co-op 32.

DETAILED DESCRIPTION OF THE NEW CULTIVAR

Figure 1:
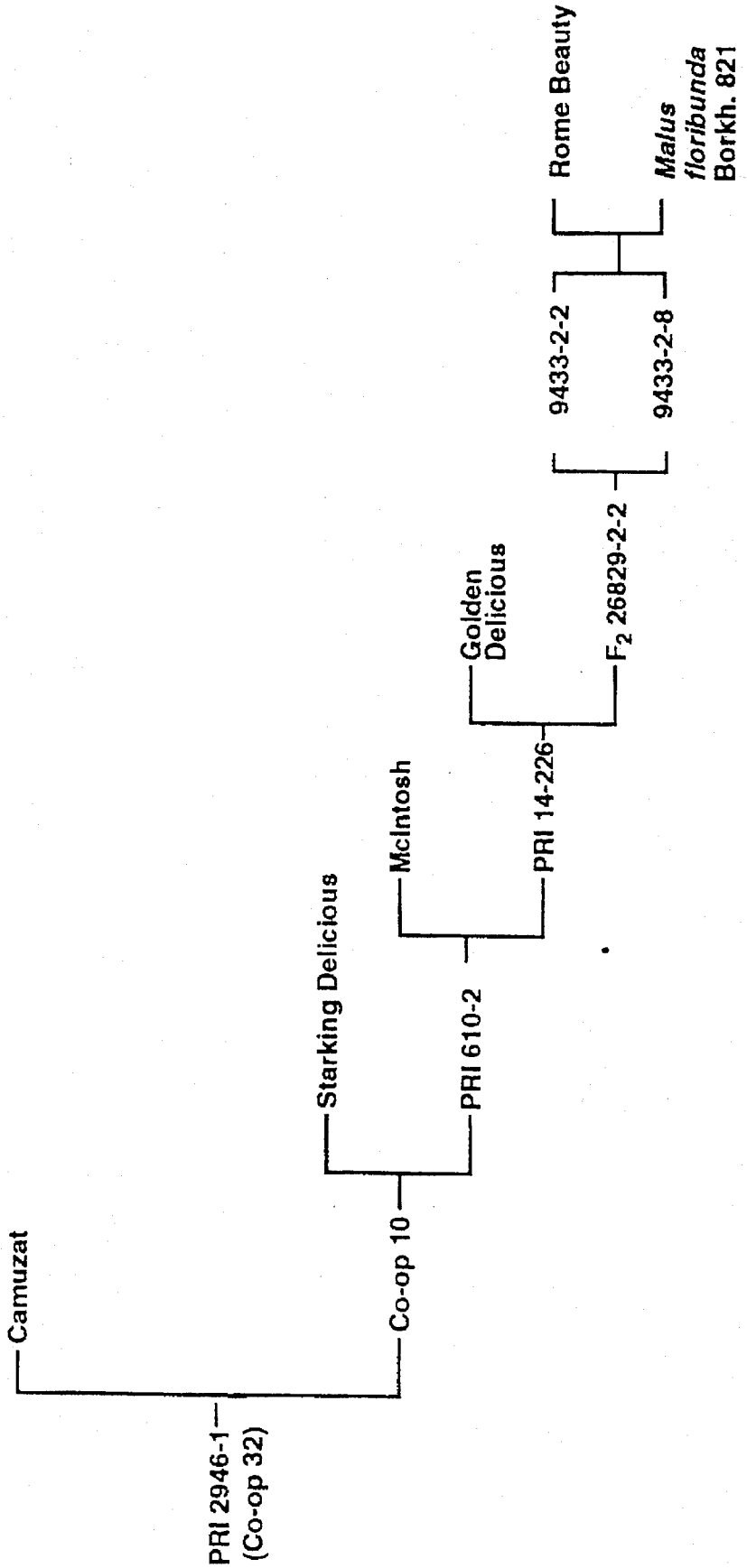
FIG. 1 is a chart showing the pedigree of Co-op 32.

FIG. 2 is a color photograph which shows a typical example of fruit and leaves of 'Co-op 32'. The following is a detailed description of the new cultivar with color designations according to The Horticultural Colour Chart by Wilson, issued by The Royal Horticultural Society of London.

FLOWERS

Corolla: Average of 49 mm in diameter at anthesis.

Petals: 15 mm×25 mm.

*Length:width ratio.*—0.62.

Color: Solferino Purple 26/1 tight bud to 26/3 in bloom stage; white at anthesis.

FRUIT

Shape: Round oblate, regular, slightly lobed.

*Length:width ratio.*—0.83.

Size: Average diameter varies from 64 to 70 mm up to 79 mm in some locations.

Color: Sap Green (62/2) when immature becoming whitish and then coloring to Lemon Yellow (4/3 to 4/2). May be blushed on sun-exposed cheek.

Skin: Very smooth, waxy, thin to medium thickness, inconspicuous lenticels.

Stem: Medium size and thickness, acute.

Basin: Medium depth, medium breadth, rounded, wavy to lobed.

Calyx: Recurved.

*Tube.*—Conical, median.

Core lines: Clasping.

Core: Median, closed.

Carpels: Emarginate, smooth.

Seeds: Full complement, acute.

Flesh:

*Texture.*—Crisp, slightly breaking yet melting, medium to fine grained; moderate browning upon exposure to air.

*Quality.*—Mild acid to sweet, slightly spice, moderately rich, full flavor, very good to excellent for season.

*Color.*—White when immature, Lemon Yellow (4/3) to paler when mature.

Maturity season: Ripens July 21 to August 4 in Lafayette, Ind. depending on season, 1.5 weeks after 'Lodi' and 'Yellow Transparent', 4.5 weeks before 'Prima', 8.5 weeks before 'Delicious'.

On-tree storage: Hangs until overripe although early ripening fruit will drop before main crop is ripe.

Keeping quality: Maintains quality and texture 4 to 6 weeks at 1° C.

Use: Early summer dessert apple.

TREE

Growth habit: Moderate vigor, round top, spreading, good crotch angles, some blindwood at the base of branches, semi-spur type bearing habit with limber wood that has some tendency to droop under a heavy crop load. Tendency to set fruit heavily on second-year old wood.

Leaves: Ovate to oval, serrate to double serrate, apex acute, base rounded.

*Length to width ratio.*—1.39.

Pruning/training requirements: Limber wood on young tress may require heading; should be trained as other standard semi-spur trees.

Branch angles: Commercially desirable branch angles, 70 to 90 degrees with little tendency for bark inclusions in crotch.

Pollination: Requires cross pollination for optimum yields.

Productivity: Moderately productive.

Thinning: Will require thinning to achieve optimum size.

Bark: Current-year stems are Moroon (1030/2) on sun-exposed surface, Pea Green (61) on underside. Lenticels on one-year old wood are raised, about 1 mm, Apricot 609/3; lenticels on 5 year old trunks are rough, about up to 1×7 mm, commonly 1×4 mm, Apricot (609/1).

We claim:

1. A new and distinct apple tree as shown and described, characterized by resistance to apple scab, fire blight, powdery mildew, and cedar-apple rust, and early season yellow apple about 1.5 weeks after 'Yellow Transparent' and 'Lodi' with very good dessert quality based on flavor and crisp breaking flesh, and excellent storage ability for an early apple.

* * * * *

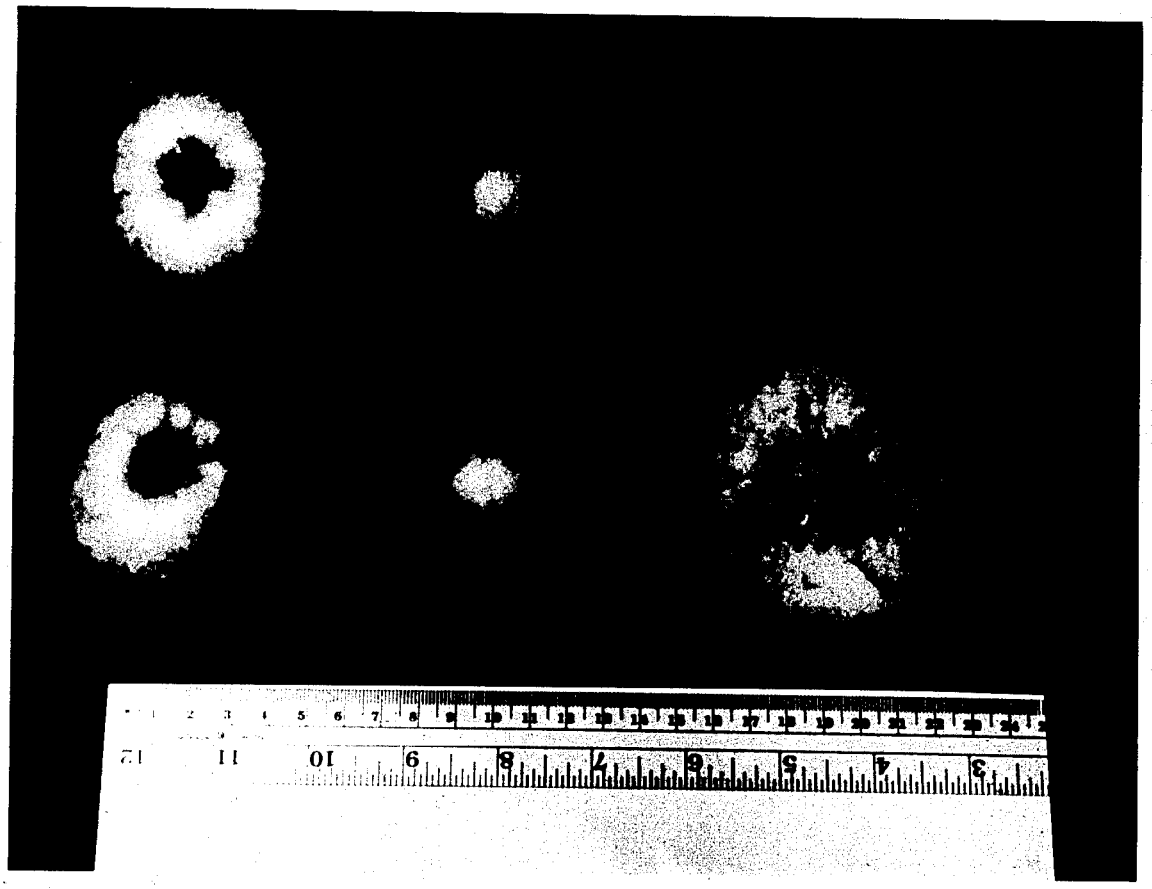

UNITED STATES PATENT AND TRADEMARK OFFICE

CERTIFICATE OF CORRECTION

PATENT NO. : PP09881

DATED : May 6, 1997

INVENTOR(S) : Jules Janick et al.

It is certified that error appears in the above-identified patent and that said Letters Patent is hereby corrected as shown below:

On the title page, item [22] delete "Dec. 11, 1995" and insert --Aug. 19, 1994--.

Signed and Sealed this

Twenty-fifth Day of August, 1998

*Attest:*

*Attesting Officer*

BRUCE LEHMAN

*Commissioner of Patents and Trademarks*